United States Patent [19]

Hertenstein et al.

[11] Patent Number: 4,536,509

[45] Date of Patent: Aug. 20, 1985

[54] 1,1-DIARYL-2-AZOLYLETHANES AND PREPARATIONS CONTAINING THESE COMPOUNDS

[75] Inventors: Ulrich Hertenstein, Leitershofen; Hilmar Mildenberger, Kelkheim; Burkhard Sachse, Kelkheim; Peter Hartz, Kelkheim, all of Fed. Rep. of Germany

[73] Assignee: Hoechst Aktiengesellschaft, Fed. Rep. of Germany

[21] Appl. No.: 585,621

[22] Filed: Mar. 7, 1984

Related U.S. Application Data

[63] Continuation of Ser. No. 381,837, May 25, 1982, abandoned.

[30] Foreign Application Priority Data

Jun. 1, 1981 [DE] Fed. Rep. of Germany ....... 3121676

[51] Int. Cl.³ .................... A01N 43/64; A01N 43/50; C07D 249/08
[52] U.S. Cl. ........................................ 514/383; 71/92; 548/325; 548/378; 548/373; 548/341; 548/101; 548/152; 548/217; 544/132; 546/276
[58] Field of Search ....................... 548/262; 424/269; 71/92

[56] References Cited

U.S. PATENT DOCUMENTS

| | | | |
|---|---|---|---|
| 4,115,578 | 9/1978 | Miller et al. | ......................... 548/338 |
| 4,275,071 | 6/1981 | Nardi et al. | ......................... 542/400 |

FOREIGN PATENT DOCUMENTS

| | | | |
|---|---|---|---|
| 867245 | 11/1978 | Belgium | ............................. 548/262 |
| 37049 | 10/1981 | European Pat. Off. | ............ 424/269 |

*Primary Examiner*—Alton D. Rollins
*Attorney, Agent, or Firm*—Connolly & Hutz

[57] ABSTRACT

Substituted ethanols of the general formula

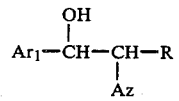

in which $Ar_1$ is a carbocyclic or heterocyclic ring and Az is a triazolyl, benzimidazolyl, pyrazolyl or imidazolyl radical, are reacted with aryl hydrocarbons $Ar_2$—H, in which $Ar_2$ has the same meaning as $Ar_1$, in the presence of an acidic catalyst, to give 1,1-diaryl-2-azolylethanes.

The substances, which, apart from the imidazolyl derivatives, are new, can be used as biocides, in particular fungicides.

11 Claims, No Drawings

1,1-DIARYL-2-AZOLYLETHANES AND PREPARATIONS CONTAINING THESE COMPOUNDS

This is a continuation of application Ser. No. 381,837, filed May 25, 1982, and now abandoned.

The invention relates to new 1,1-diaryl-2-azolylethyl derivatives, a process for the preparation of this substance class, and their use as biocides, in particular as fungicides.

It is known that compounds from the class comprising the 1,1-diaryl-2-imidazolylethanes possess fungicidal properties (U.S. Pat. No. 4,115,578 and German Offenlegungsschrift No. 2,604,047). However, more detailed data concerning their activity, in particular when low amounts are used, their spectrum of action, and the focal point of their action are not available.

It has been found that certain 1,1-diaryl-2-azolylethanes not described hitherto surprisingly have a substantially higher fungicidal power compared to those already known, in particular against rust and powdery mildew, are herbicidally active, and can also be employed as antimycotics.

The invention therefore relates to new 1,1-diaryl-2-azolylethanes of the general formula (I)

$$Ar_1-\underset{Z}{\underset{|}{CH}}-Ar_2 \qquad (I)$$

in which $Ar_1$ and $Ar_2$ represent identical or different radicals which have the meaning of naphth-1-yl or naphth-2-yl, tetrahydronaphth-1-yl or tetrahydronaphth-2-yl, indan-5-yl, five-membered or six-membered or benzo-fused five-membered or six-membered heterocyclic rings having up to two hetero-atoms which can be N, O or S, or in particular have the meaning of radicals of the formula (II)

(II)

and in this formula, $R^1$ to $R^5$ are identical or different and preferably represent hydrogen, halogen, $CF_3$, $C_1$- to $C_8$-alkyl, $C_2$- to $C_8$-alkenyl, $C_5$- or $C_6$-cycloalkyl, $C_1$- to $C_6$-alkoxy or $C_2$- or $C_6$-alkenoxy, or also phenoxy or phenyl radicals which can be substituted by up to 5 halogen atoms, preferably chlorine atoms, but in particular represent H, Cl, Br and $C_1$- to $C_8$-alkyl.

Z is a radical of the formula (III)

$$R^6-\underset{Az}{\underset{|}{CH}}- \qquad (III)$$

in which $R^6$ denotes hydrogen or an alkyl or alkenyl radical which has up to 8, preferably 1 or 2, C atoms and which can be substituted by up to two alkoxy or amino groups which have 1 or 2 C atoms and which may also be different, but in particular is H, methyl or ethyl.

Az particularly represents 1,2,4-triazol-1-yl or 1,2,4-triazol-4-yl, or can also be benzimidazol-1-yl or pyrazol-1-yl.

The salts, complex salts and quaternization products of 1,1-diaryl-2-azolylethanes are also included.

The new compounds are obtained from compounds which carry an alcoholic OH group and are of the formula $$Ar_1-\underset{Az}{\underset{|}{\overset{\overset{OH}{|}}{CH}}}-CH-R^6 \qquad (V)$$

in which $Ar_1$, $R^6$ and Az have the meanings given above, by reaction with aryl hydrocarbons of the formula (VI)

$$H-Ar_2 \qquad (VI)$$

in which $Ar_2$ is one of the radicals given above.

The reaction is carried out in the temperature range from $-15°$ to $+150°$ C., preferably from $-10°$ to $110°$ C., in the presence of an acidic catalyst, if appropriate in the presence of a diluent. In this context, acidic catalysts are understood as meaning the conventional Friedel-Crafts catalysts, as described—like the suitable diluents—for example in Houben-Weyl, Methoden der org. Chemie, Vol. 7/2a, pages 17 to 21. Tetrachloroethane and aluminum trichloride are preferred. 1.1 to 2.5 equivalents of the catalyst and at least one equivalent of the aryl hydrocarbon $H-Ar_2$, relative to the compound of the formula (V), are employed.

Examples of starting compounds of the formula (V) which are suitable for the preparation of the 1,1-diaryl-2-azolylethanes are: 1-(2,4-dichlorophenyl)-1-hydroxy-2-(1,2,4-triazol-1-yl)-ethane, 1-(2,4-dichlorophenyl)-1-hydroxy-2-(1,2,4-triazol-1-yl)-propane, 1-(2,4-dichlorophenyl)-1-hydroxy-2-(1,2,4-triazol-1-yl)-hexane, 1-(2,4-dichlorophenyl)-1-hydroxy-2-(1,2,4-triazol-1-yl)-octane, 1-(2,4-dichlorophenyl)-1-hydroxy-2-(imidazolyl-1-yl)-ethane, 1-(2,4-dichlorophenyl)-1-hydroxy-2-(imidazolyl-1-yl)-propane, 1-(2,4-dichlorophenyl)-1-hydroxy-2-(imidazolyl-1-yl)-hexane, 1-(2,4-dichlorophenyl)-1-hydroxy-2-(imidazolyl-1-yl)-octane, 1-(3,4-dichlorophenyl)-1-hydroxy-2-(1,2,4-triazol-1-yl)-ethane, 1-(2,5-dichlorophenyl)-1-hydroxy-2-(1,2,4-triazol-1-yl)-ethane, 1-(2-methyl-4-chlorophenyl)-1-hydroxy-2-(1,2,4-triazol-1-yl)-ethane, 1-(4-methoxyphenyl)-1-hydroxy-2-(1,2,4-triazol-1-yl)-ethane, 1-(4-phenylphenyl)-1-hydroxy-2-(1,2,4-triazol-1-yl)-ethane, 1-phenyl-1-hydroxy-2-(1,2,4-triazol-1-yl)-3-methoxypropane, 1-phenyl-1-hydroxy-2-(1,2,4-triazol-1-yl)-4-methoxy-butane, 1-phenyl-1-hydroxy-2-(imidazol-1-yl)-4-(2,6-dimethylmorpholin-4-yl)-butane and 1-pentamethylphenyl-1-hydroxy-2-(1,2,4-triazol-1-yl)-propane.

The aromatics of the formula $H-Ar_2$ (VI) are understood as meaning, for example: chlorobenzene, bromobenzene, 1,3-dichlorobenzene, 1,2-dichlorobenzene, 1,4-dichlorobenzene, toluene, xylene, mesitylene, 3-chlorotoluene, 4-chlorotoluene, anisole, pyridine, thiophene, benzothiophene, benzoxazole, benzthiazole, naphthalene, tetrahydronaphthalene and indane.

In the synthesis, the procedure is carried out, in particular, as follows: the compounds of the formula (V), the aryl hydrocarbon $H-Ar_2$ (VI) and, if appropriate, a diluent are initially introduced, and the catalyst is slowly metered in at approx. $-10°$ C. The mixture is allowed to reach room temperature in the course of 30 minutes, and is then heated until the evolution of gas begins. When this has ended, the mixture is heated for a further 30 minutes, allowed to cool to room temperature, poured onto ice, and rendered strongly alkaline with 50% strength NaOH, while cooling with ice, and the organic phase is then worked up in the conventional manner.

Using the same method, the products belonging to the same compound class and described in German Offenlegungsschrift No. 2,604,047 and U.S. Pat. No. 4,115,578 can also be prepared; these are those compounds of the formula (I) in which, in the radical Z the structure of which is illustrated by formula (III), Az represents an imidazolyl radical of the formula (IV)

in which Y denotes $C_1$- to $C_4$-alkyl, a halogen atom or nitro, and n can be 0 to 3, which compounds are obtainable by the process described in these publications only in minimal yields, via 8 reaction steps. In contrast, the process according to the invention is carried out in 4 stages with a total yield of more than 50%.

The course of the reaction leading to the products according to the invention may be illustrated by the example, given below, of the reaction of 1,3-dichlorobenzene with 1-(4-chlorophenyl)-1-hydroxy-2-(1,2,4-triazol-1-yl)-ethane:

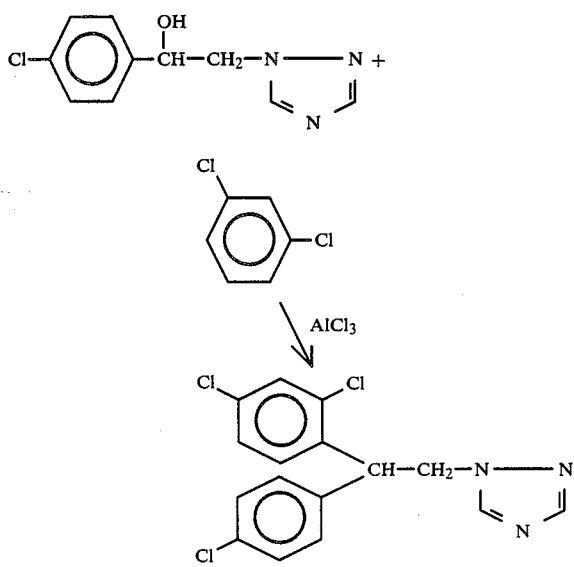

This is surprising and could not be foreseen, since, under the process conditions, it was to be expected that water would be split off to give ω-(1,2,4-triazol-1-yl)-styrene, as is known to take place in the case of 1-phenylethanolene [Journ. Am. Chem. Soc. 73 (1951), page 455; and Journ. Chem. Soc. 87, page 672], and splitting off of triazole, or a polymerization, are also possible.

The 1,1-diaryl-2-azolylethanes according to the invention can occur in the E form and Z form. As basic compounds, they are furthermore capable of forming salts, complex salts and quaternization products. Salts of organic and inorganic acids may be mentioned, such as, for example, acetates, fumarates, oxalates, benzoates, nitrates, bromides, chlorides and sulfates, salts of naphthalenesulfonic acids, complexes with metals of group 1b, 2b, 4b or 8b of the periodic table, for example copper, zinc and tin, and quaternization products with alkyl halides and phenacyl halides. The preparation of such compounds is effected according to generally customary methods.

The compounds according to the invention, of the formula I, are distinguished by an outstanding fungicidal action, in particular, for example, when used in plant protection. In this context, fungal pathogens which have already penetrated the plant tissue can be successfully controlled by curative measures. This is particularly important and advantageous in the case of those fungal diseases which, after infection has occurred, can no longer be effectively controlled with the fungicides otherwise customarily used. The spectrum of action of the claimed compounds includes, for example, in addition to various rust species, Phytophthora infestans, Plasmopara viticola and Piricularia oryzae, but in particular powdery mildew fungi in the cultivation of fruit, vegetables, cereal and decorative plants. The excellent action of the compounds against powdery mildew species which are resistant to benzimidazole derivatives (for example Benomyl and Carbendazim) should be particularly singled out.

Moreover, the substances are suitable for use in industrial fields, for example as wood preservatives, as preservatives in paints, in cooling lubricants for metalworking, or as preservatives in drilling oils and cutting oils.

The agents can be used as wettable powders, emulsifiable concentrates, atomizable solutions, dusting agents, dressing agents, dispersions, granules or microgranules, in the conventional preparations.

Wettable powders are understood as meaning preparations which are uniformly dispersible in water and which also contain, in addition to the active compound and in addition to any diluent or inert substance, wetting agents, for example polyoxyethylated alkylphenols, polyoxyethylated fatty alcohols, alkyl sulfonates or alkylphenyl sulfonates, and dispersants, for example sodium ligninsulfonate, sodium 2,2'-dinaphthylmethane-6,6'-disulfonate, sodium dibutylnaphthalene sulfonate or even sodium oleolylmethyl taurate. Their preparation is effected in a conventional manner, for example by grinding and mixing the components.

Emulsifiable concentrates can be prepared, for example, by dissolving the active compound in an inert organic solvent, for example butanol, cyclohexanone, dimethylformamide, xylene or even high-boiling aromatics or hydrocarbons, with the addition of one or more emulsifiers. In the case of liquid active compounds, the solvent constituent can also be either completely or partially dispensed with. Examples of emulsifiers which can be used are: calcium salts of alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitane fatty acid esters, polyoxyethylene sorbitane fatty acid esters or polyoxyethylene sorbitol esters.

Dusting agents are obtained by grinding the active compound with finely divided solid substances, for example talc, natural clays, such as kaolin, bentonite or pyrophillite, or diatomaceous earth.

Granules can be prepared either by spraying the active compound onto absorptive, granulated inert material, or by applying active compound concentrations onto the surface of carriers, such as sand or kaolinites, or of granulated inert material by means of binders, for example polyvinyl alcohol, sodium polyacrylic or even mineral oils. It is also possible to granulate suitable active compounds in the manner customary for the preparation of fertilizer granules—if desired as a mixture with fertilizers.

In wettable powders, the active compound concentration is, for example, about 10 to 90% by weight, and the residual amount up to 100% by weight comprises conventional formulation constituents. In the case of emulsifiable concentrates, the active compound concentration can be about 10 to 80% by weight. Dust-like formulations contain at most 5 to 20% by weight of active compound, and atomizable solutions contain about 1 to 20% by weight. In the case of granules, the active compound content depends in part on whether the active compound is present in liquid or solid form, and which granulation auxiliaries, fillers, etc. are used.

In addition, the active compound formulations mentioned contain, if appropriate, the adhesives, wetting agents, dispersants, emulsifiers, penetrating agents, solvents, fillers or carriers customarily used in the particular case.

For use, the concentrates present in the commercial form are diluted in the conventional manner if appropriate, for example in the case of wettable powders, emulsifiable concentrates and dispersions, and also in the case of some of the microgranules, by means of water. Dust-like and granulated preparations, and atomizable solutions, are customarily no longer diluted with further inert substances before use.

Mixtures or mixed formulations with other active compounds, such as, for example, insecticides, acaricides, herbicides, fertilizers, growth regulators or further fungicides are also possible if required, and synergistic increases in action can also be achieved in certain circumstances.

Some formulation examples are mentioned below:

A dusting agent is obtained by mixing 10 parts by weight of active compound and 90 parts by weight of talc as the inert substance, and comminuting the mixture in a hammer mill.

A wettable powder which is readily dispersible in water is obtained by mixing 25 parts by weight of active compound, 64 parts by weight of kaolin-containing quartz as the inert substance, 10 parts by weight of potassium ligninsulfonate and 1 part by weight of sodium oleoylmethyl taurate as the wetting agent and dispersant, and grinding the mixture in a pinned disk mill.

A dispersion concentrate which is readily dispersible in water is prepared by mixing 20 parts by weight of active compound with 6 parts by weight of alkylphenol polyglycol ether (Triton X 207), 3 parts by weight of isotridecanol polyglycol ether (8 ethylene oxide units) and 71 parts by weight of paraffinic mineral oil (boiling range, for example, approx. 255° to above 377° C.), and grinding the mixture in an attrition ball mill to a fineness of less than 5 microns.

An emulsifiable concentrate can be prepared from 15 parts by weight of active compound, 75 parts by weight of cyclohexanone as the solvent and 10 parts by weight of oxyethylated nonylphenol (10 ethylene oxide units) as the emulsifier.

PREPARATION EXAMPLES

EXAMPLE 1

1,1-Diphenyl-2-(1,2,4-triazol-1-yl)-ethane

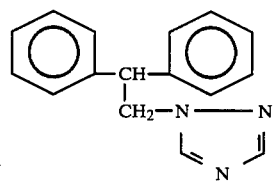

26.7 g (0.2 mole) of AlCl$_3$ were added in portions to a solution of 18.9 g (0.1 mole) of 1-phenyl-2-(1,2,4-triazol-1-yl)-ethanol in 50 ml of benzene and 50 ml of 1,2-dichloroethane at $-10°$ C. Thereafter, the mixture was warmed to room temperature in the course of 30 minutes, and was then heated to 80° C., until the evolution of gas was no longer observed. The mixture was poured onto 200 ml of ice-water, the organic phase was separated off and concentrated, and the residue was triturated with diisopropyl ether. Yield 21.4 g (86%), m.p. 107°–108° C.

C$_{16}$H$_{15}$N$_3$ calculated: C 77.1%, H 6.0%, N 16.9%; found: C 77.0%, H 5.9%, N 17.2%.

$^1$H-NMR (CDCl$_3$, TMS internal): $\delta = 4.40$–$4.82$(m,3H, CH—CH$_2$) 7.00–7.35 (m, 10H, aromatic) 7.55 (s, 1H, azole) 7.88 ppm (s, 1H, azole)

EXAMPLE 2

1-(4-Methylphenyl)-1-phenyl-2-(1,2,4-triazol-1-yl)-ethane

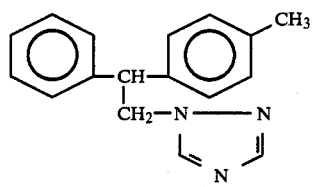

20 g (0.15 mole) of AlCl$_3$ were added in portions to a solution of 18.9 g (0.1 mole) of 1-phenyl-2-(1,2,4-triazol-1-yl)-ethanol in 50 ml of toluene and 50 ml of 1,2-dichloroethane at $-10°$ C. Thereafter, the mixture was heated to 80° C., until the evolution of gas was no longer observed. The mixture was poured onto 200 ml of ice-water, the organic phase was separated off and concentrated, and the residue was triturated with diisopropyl ether. Yield 23.8 g (90%), m.p. 98°–100° C.

C$_{17}$H$_{17}$N$_3$ calculated: C 77.6%, H 6.5%, N 16.0%; found: C 77.3%, H 6.5%, N 15.9%.

$^1$H-NMR (CDCl$_3$, TMS internal):=2.26 (s, 3H, CH$_3$), 4.38–4.80 (m, 3H, CH—CH$_2$), 6.95–7.25 (m, 9H, aromatic), 7.50 (s, 1H, azole), 7.85 ppm (s, 1H, azole).

EXAMPLES 3 TO 40

The compounds of the formula

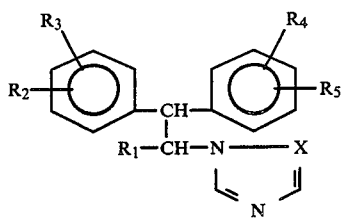

which are listed in Table 1 below were prepared by the procedure of Example 1:

EXAMPLE I

Wheat plants in the 3-leaf stage were strongly inoculated with conidia of wheat powdery mildew (*Erysiphe graminis*) and were placed in a greenhouse at 20° C. and a relative atmospheric humidity of 90–95%. 3 days after inoculation, the plants were sprayed, until dripping wet, with the compounds listed in Table I, in the active compound concentrations of 500, 250, 125, 60 and 30 mg/liter of spray liquor. For comparison, comparative agent B was employed in an analogous manner. After an incubation time of 10 days, the plants were examined for infection with wheat powdery mildew. The degree of infection was expressed as a percentage of the infected leaf area, relative to the untreated, infected control plants (=100% infection). The result is summarized in Table I.

Starting materials

| Example No. | $R_1$ | $R_2$ | $R_3$ | X | $R_4$ | $R_5$ | physical constants/ b.p. (°C.) and pressure (mbar) or melting point |
|---|---|---|---|---|---|---|---|
| 3 | H | H | H | N | H | 4-C(CH$_3$)$_3$ | 187–98/0.001 |
| 4 | H | H | H | N | H | 4-OCH$_3$ | 192–205/0.05 |
| 5 | H | H | H | N | 2-CH$_3$ | 4-CH$_3$ | 160–70/0.0007 |
| 6 | H | H | H | N | 2-CH$_3$ | 5-CH$_3$ | 175–82/0.001 |
| 7 | H | H | H | N | H | 4-Br | 208/0.005 |
| 8 | H | H | H | N | H | 4-Cl | 175–9/0.002 |
| 9 | H | H | 4-Cl | N | H | 4-Br | 208–19/0.004 |
| 10 | H | H | 4-Cl | N | H | 4-Cl | 129–33 |
| 11 | H | H | H | N | 2-Cl | 4-Cl | 178–88/0.0001 |
| 12 | H | H | 4-Cl | N | 2-Cl | 4-Cl | 215–221/0.004 |
| 13 | H | H | 4-Cl | N | 2-CH$_3$ | 4-CH$_3$ | 215–222/0.005 |
| 14 | H | H | 4-Cl | N | 2-CH$_3$ | 5-CH$_3$ | 180–90/0.0001 |
| 15 | H | H | 4-Cl | N | H | 4-CH$_3$ | 110–3 |
| 16 | H | H | 4-Cl | N | H | 4-OH | 58–60 |
| 17 | H | H | 4-Cl | N | H | 4-OCH$_3$ | 170–8/0.0006 |
| 18 | CH$_3$ | H | H | N | H | H | 95–6 |
| 19 | CH$_3$ | H | H | N | H | 4-Br | 135–40 |
| 20 | CH$_3$ | H | H | N | H | 4-Cl | 180–3/0.003 |
| 21 | CH$_3$ | H | H | N | H | 4-CH$_3$ | 178–81/0.003 |
| 22 | CH$_3$ | H | H | N | H | 4-OCH$_3$ | 90 |
| 23 | CH$_3$ | H | H | N | 2-CH$_3$ | 4-CH$_3$ | 185–7/0.001 |
| 24 | CH$_3$ | H | H | N | 2-CH$_3$ | 5-CH$_3$ | 166–74/0.0008 |
| 25 | C$_2$H$_5$ | H | H | N | H | H | 113–8 |
| 26 | C$_2$H$_5$ | H | H | N | H | 4-CH$_3$ | 160–74/0.0007 |
| 27 | C$_2$H$_5$ | H | H | N | H | 4-OCH$_3$ | 153–6 |
| 28 | C$_2$H$_5$ | H | H | N | H | 4-Cl | 178–82/0.0007 |
| 29 | C$_2$H$_5$ | H | 4-Br | N | H | 4-Br | 215–26/0.01 |
| 30 | C$_2$H$_5$ | H | 4-CH$_3$ | N | H | 4-C(CH$_3$)$_3$ | 144–7 |
| 31 | C$_2$H$_5$ | H | 4-CH$_3$ | N | H | 4-CH$_3$ | 109–13 |
| 32 | C$_2$H$_5$ | H | 4-CH$_3$ | N | H | 4-OCH$_3$ | 202–16/0.001 |
| 33 | C$_2$H$_5$ | H | H | N | 2-CH$_3$ | 4-CH$_3$ | 160–8 |
| 34 | C$_2$H$_5$ | H | H | N | 2-CH$_3$ | 5-CH$_3$ | 121–6 |
| 35 | C$_2$H$_5$ | H | 4-CH$_3$ | N | 2-CH$_3$ | 4-CH$_3$ | 121–3 |
| 36 | C$_2$H$_5$ | H | 4-CH$_3$ | N | 2-CH$_3$ | 5-CH$_3$ | 175–8 |
| 37 | H | 2-Cl | 4-Cl | CH | H | H | 203–8/0.005 |
| 38 | H | 2-Cl | 4-Cl | CH | H | 4-Cl | 207–24/0.005 |
| 39 | H | 2-Cl | 4-Cl | CH | H | 4-CH$_3$ | 208–15/0.005 |
| 40 | H | 2-Cl | 4-Cl | CH | 2-CH$_3$ | 5-CH$_3$ | 207–17/0.005 |

BIOLOGICAL EXAMPLES

In the examples which follow, the letters A, B, C and D represent the commercially available comparative agents mentioned below and containing known fungicidal active compounds:

A: Methyl 1-(butylcarbamoyl)-benzimidazole-2-carbamate (Benomyl)
B: N-Tridecyl-2,6-dimethylmorpholine (tridemorph)
C: 5-Methyl-1,2,4-triazolo-[3,4-b]-benzothiazole (tricyclazole)
D: 5,6-Dihydro-2-methyl-1,4-oxathiine-3-carboxanilide-4,4-dioxide

TABLE I

| Compound according to Example No. | Leaf area, in %, infected with wheat powdery mildew at mg of active compound/l of spray liquor | | | | |
|---|---|---|---|---|---|
| | 500 | 250 | 125 | 60 | 30 |
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |

TABLE I-continued

| Compound according to Example No. | Leaf area, in %, infected with wheat powdery mildew at mg of active compound/l of spray liquor | | | | |
|---|---|---|---|---|---|
| | 500 | 250 | 125 | 60 | 30 |
| 5 | 0 | 0 | 0 | 0 | 0 |
| 6 | 0 | 0 | 0 | 0 | 0 |
| 7 | 0 | 0 | 0 | 0 | 0 |
| 8 | 0 | 0 | 0 | 0 | 0 |
| 9 | 0 | 0 | 0 | 0 | 0 |
| 10 | 0 | 0 | 0 | 0 | 0 |
| 11 | 0 | 0 | 0 | 0 | 0 |
| 12 | 0 | 0 | 0 | 0 | 0 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 0–3 | 3 |
| 17 | 0 | 0 | 0 | 0–3 | 3 |
| 18 | 0 | 0 | 0 | 0–3 | 3 |
| 19 | 0 | 0 | 0 | 0 | 0 |
| 20 | 0 | 0 | 0 | 0 | 0 |
| 21 | 0 | 0 | 0 | 0 | 0 |
| 22 | 0 | 0 | 0 | 0–3 | 3 |
| 23 | 0 | 0 | 0 | 0 | 0–3 |
| 24 | 0 | 0 | 0 | 0 | 0 |
| 25 | 0 | 0 | 0 | 0 | 0 |
| 26 | 0 | 0 | 0 | 0 | 0 |
| 27 | 0 | 0 | 0 | 0 | 0 |
| 28 | 0 | 0 | 0 | 0 | 0 |
| 29 | 0 | 0 | 0 | 0 | 0 |
| 30 | 0 | 0 | 0 | 0 | 0 |
| 31 | 0 | 0 | 0 | 0 | 0 |
| 32 | 0 | 0 | 0 | 0 | 0 |
| 33 | 0 | 0 | 0 | 0 | 0 |
| 34 | 0 | 0 | 0 | 0 | 0 |
| 35 | 0 | 0 | 0 | 0 | 0 |
| 36 | 0 | 0 | 0 | 0 | 0 |
| Comparative agent B | 3 phytotoxic | 5 phytotoxic | 10 | 15 | 25 |
| Untreated, infected plants | | 100 | | | |

EXAMPLE II

Rice plants in the 4-leaf stage were sprayed, until dripping wet, with the compounds given in Table II, in concentrations of 500, 250 and 120 mg of active compound per liter of spray liquor. After the spray coating had dried on, the plants were sprayed uniformly with a spore suspension of *Piricularia oryzae,* and were placed for 48 hours in a dark climatically controlled chamber at 25° C. and 100% relative atmospheric humidity. Thereafter, the plants were kept in a greenhouse at 25° C. and 85% relative atmospheric humidity, and were examined, 14 days after inoculation, for infection with *Piricularia oryzae.* The degree of infection was expressed as a percentage of the infected leaf area, relative to the untreated, infected control plants (=100% infection).

TABLE II

| Compound according to Example No. | % infected leaf area at mg of active compound/liter of spray liquor | | |
|---|---|---|---|
| | 500 | 250 | 120 |
| 1 | 0 | 0 | 0–3 |
| 2 | 0 | 0 | 0–3 |
| 3 | 0 | 0 | 0 |
| 4 | 0 | 0 | 0–3 |
| 5 | 0 | 0 | 0–3 |
| 6 | 0 | 0 | 0 |
| 10 | 0 | 0 | 0–3 |
| 11 | 0 | 0 | 0 |
| 12 | 0 | 0 | 0–3 |
| 13 | 0 | 0 | 0 |
| 15 | 0 | 0 | 0–3 |
| 17 | 0 | 0 | 0–3 |
| 18 | 0 | 0 | 0–3 |
| 19 | 0 | 0 | 0 |
| 20 | 0 | 0 | 0–3 |
| 22 | 0 | 0 | 0–3 |
| 23 | 0 | 0 | 0–3 |
| 24 | 0 | 0 | 0–3 |
| 32 | 0 | 0 | 0–3 |
| Comparative agent C | 0 | 3 | 5 |
| Untreated, infected plants | | 100 | |

EXAMPLE III

Wheat plants were treated, until dripping wet, with the compounds mentioned in Table III, amounts of 500, 250, 120 and 60 mg/liter of spray liquor being used. After the coating of active compound had dried off, the plants were strongly inoculated with spores of wheat brown rust (*Puccinia triticina*), and were placed for 24 hours in a climatically controlled chamber at 20° C. and 100% relative atmospheric humidity. Thereafter, the plants were placed in a greenhouse and were examined here, 14 days after inoculation, for infection with wheat brown rust. D served as the comparative agent.

TABLE III

| Compound according to Example No. | Leaf area, in %, infected with wheat brown rust at mg of active compound per liter of spray liquor | | | |
|---|---|---|---|---|
| | 500 | 250 | 120 | 60 |
| 8 | 0 | 0 | 0 | 0 |
| 10 | 0 | 0 | 0 | 0 |
| 14 | 0 | 0 | 0 | 0 |
| 15 | 0 | 0 | 0 | 0 |
| 16 | 0 | 0 | 0–3 | 3 |
| 17 | 0 | 0 | 0 | 0 |
| 18 | 0 | 0 | 0 | 0–3 |
| 19 | 0 | 0 | 0 | 0 |
| 20 | 0 | 0 | 0 | 0 |
| 22 | 0 | 0 | 0–3 | 3 |
| 23 | 0 | 0 | 0 | 0–3 |
| 24 | 0 | 0 | 0–3 | 3 |
| 1 | 0 | 0 | 0 | 0 |
| 13 | 0 | 0 | 0 | 0–3 |
| 12 | 0 | 0 | 0 | 0 |
| 11 | 0 | 0 | 0 | 0 |
| 2 | 0 | 0 | 0–3 | 3 |
| 3 | 0 | 0 | 0–3 | 3 |
| 4 | 0 | 0 | 0–3 | 3 |
| 5 | 0 | 0 | 0–3 | 3 |
| 6 | 0 | 0 | 0–3 | 3 |
| 7 | 0 | 0 | 0 | 0 |
| 9 | 0 | 0 | 0 | 0 |
| Comparative agent D | 5 | 10 | 15 | 35 |
| Untreated, infected plants | | 100 | | |

As industrial biocides, some compounds also showed a good, broadly active fungicidal action and, in part, also a bactericidal action, in this respect in particular against *Bacillus subtilis:*

EXAMPLE IV

Pieces of mycelium (0.5 cm diameter) of the fungus *Poria monticola* were applied to the center of the nutrient substrata (biomalt agar for fungi) in Petri dishes; the claimed compounds, in the concentrations given in Table IV, had been added beforehand to the agar in the liquid state. 8 days after the inoculation of the plates, the diameter of the fungal mycelium on the agar was measured, and the inhibition of growth caused by the preparations was expressed as a percentage, relative to the control (=inoculated agar without the addition of active compound=0% inhibition).

TABLE IV

| Compounds according to Example | Inhibition of *Poria monticola* in % at mg of active compound/liter of agar | | | | | |
|---|---|---|---|---|---|---|
| | 100 | 50 | 10 | 5 | 1 | 0.5 |
| 1 | 100 | 100 | 80 | 50 | 0 | |
| 2 | 100 | 100 | 80 | 50 | 0 | |
| 3 | 100 | 100 | 50 | 50 | 0 | |
| 4 | 100 | 100 | 50 | 0 | 0 | |
| 5 | 100 | 100 | 80 | 80 | 0 | |
| 6 | 100 | 100 | 100 | 100 | 100 | 50 |
| 7 | 100 | 100 | 100 | 100 | 100 | 50 |
| 8 | 100 | 100 | 100 | 100 | 50 | 50 |
| 9 | 100 | 100 | 100 | 80 | 0 | |
| 10 | 100 | 100 | 100 | 100 | 80 | 50 |
| 11 | 100 | 100 | 100 | 100 | 100 | 80 |
| 12 | 100 | 100 | 100 | 80 | 0 | |
| 13 | 100 | 100 | 100 | 80 | 0 | |
| 14 | 100 | 100 | 100 | 100 | 80 | 50 |
| 15 | 100 | 100 | 100 | 100 | 80 | 50 |
| 17 | 100 | 100 | 100 | 80 | 0 | |
| 18 | 100 | 100 | 50 | 0 | | |
| 19 | 100 | 100 | 80 | 50 | 0 | |
| 20 | 100 | 100 | 50 | 50 | 0 | |

EXAMPLE V 0.02 ml each of a spore suspension of *Ulocladium consortiale*, *Aureobasidium pullulans* and *Aspergillus niger* were applied dropwise to the nutrient substrata (biomalt agar for fungi) in Petri dishes; the claimed compounds, in the concentrations given in Table V, had been added beforehand to the agar in the liquid state. 6 days after inoculation of the plates, the diameter of the fungus colonies on the agar was measured, and the inhibition of growth caused by the preparation was expressed as a percentage, relative to the control (=inoculated agar without the addition of active compound=0% inhibition).

TABLE V

| Compounds according to Example | Inhibition of *Ulocladium consortiale*, *Aureobasidium pullulans* and *Aspergillus niger* in % at mg of active compound/liter of agar | | | | | |
|---|---|---|---|---|---|---|
| | 100 | 50 | 10 | 5 | 1 | 0.5 |
| 5 | Uc 100 | 100 | 80 | 50 | | |
| | Ap 100 | 100 | 50 | | | |
| | An 100 | 50 | 0 | | | |
| 6 | Uc 100 | 80 | 50 | | | |
| | Ap 100 | 100 | 0 | | | |
| | An 80 | 50 | 0 | | | |
| 7 | Uc 100 | 100 | 80 | 50 | | |
| | Ap 100 | 100 | 80 | 50 | | |
| | An 100 | 100 | 50 | | | |
| 8 | Uc 100 | 100 | 80 | 80 | | |
| | Ap 100 | 100 | 80 | 80 | | |
| | An 100 | 100 | 80 | 80 | | |
| 9 | Uc 100 | 100 | 80 | 50 | | |
| | Ap 100 | 100 | 100 | 80 | | |
| | An 80 | 50 | 0 | | | |
| 10 | Uc 100 | 100 | 100 | 50 | | |
| | Ap 100 | 100 | 100 | 80 | 50 | 50 |
| | An 100 | 100 | 80 | 50 | | |
| 11 | Uc 100 | 100 | 100 | 100 | 80 | 80 |
| | Ap 100 | 100 | 100 | 100 | 80 | 80 |
| | An 100 | 80 | 50 | 0 | | |
| 12 | Uc 100 | 100 | 100 | 100 | 0 | |
| | Ap 80 | 80 | 50 | 0 | | |

TABLE V-continued

| Compounds according to Example | Inhibition of *Ulocladium consortiale*, *Aureobasidium pullulans* and *Aspergillus niger* in % at mg of active compound/liter of agar | | | | | |
|---|---|---|---|---|---|---|
| | 100 | 50 | 10 | 5 | 1 | 0.5 |
| | An 100 | 100 | 50 | 0 | | |
| 13 | Uc 100 | 100 | 80 | 80 | | |
| | Ap 100 | 80 | 50 | 50 | | |
| | An 50 | 50 | 0 | | | |
| 14 | Uc 100 | 100 | 80 | 80 | | |
| | Ap 80 | 80 | 50 | 50 | | |
| | An 80 | 80 | 50 | 0 | | |
| 15 | Uc 100 | 100 | 80 | 50 | | |
| | Ap 100 | 100 | 80 | 50 | | |
| | An 80 | 80 | 50 | 0 | | |
| 20 | Uc 100 | 80 | 50 | 50 | | |
| | Ap 80 | 80 | 50 | 0 | | |
| | An 80 | 80 | 50 | 0 | | |

EXAMPLE VI 0.02 ml each of a bacteria suspension of *Bacillus subtilis* were applied dropwise to the nutrient substrata (standard—I nutrient agar for bacteria) in Petri dishes; the claimed compounds, in the concentrations given in Table VI, had been added beforehand to the agar in the liquid state. The plates inoculated with bacteria were evaluated after 4 days; in this evaluation, the inhibition of growth in comparison to the control (=inoculated agar without the addition of active compound=0% inhibition) was assessed.

TABLE VI

| Compounds according to Example | Inhibition of *Bacillus subtilis* in % at mg of active compound/liter of agar | | | | |
|---|---|---|---|---|---|
| | 100 | 50 | 10 | 5 | 1 |
| 3 | 100 | 100 | 100 | 100 | 0 |
| 5 | 100 | 100 | 50 | 0 | |
| 6 | 100 | 100 | 50 | 0 | |
| 9 | 100 | 100 | 50 | 0 | |
| 10 | 100 | 100 | 50 | 0 | |
| 12 | 100 | 100 | 100 | 50 | 0 |
| 14 | 100 | 100 | 80 | 0 | |
| 16 | 100 | 100 | 80 | 0 | |
| 19 | 100 | 100 | 50 | 0 | |
| 20 | 100 | 50 | 50 | 0 | |
| 23 | 100 | 50 | 50 | 0 | |
| 26 | 100 | 50 | 50 | 0 | |
| 29 | 100 | 100 | 50 | 0 | |
| 34 | 100 | 100 | 50 | 50 | 0 |

We claim:
1. A compound of the formula

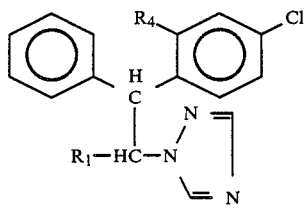

wherein $R_1$ is hydrogen or methyl, and $R_4$ is hydrogen or a chlorine atom.

2. A compound according to claim 1, wherein $R_1$ is methyl.

3. A compound according to claim 1, wherein $R_1$ is hydrogen.

4. A compound according to claim 1, wherein $R_4$ is a chlorine atom.

5. A compound according to claim 1, wherein $R_4$ is hydrogen.

6. A compound of the formula

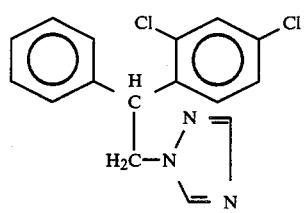

7. A compound of the formula

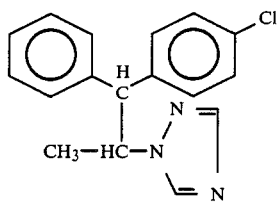

8. An active compound formulation having fungicidal, bactericidal, herbicidal, or antimycotic activity, which comprises an effective amount of at least one of the compounds of claim 1 and an adhesive, a wetting agent, a dispersant, an emulsifier, a penetrating agent, a solvent, a filler, or a carrier.

9. An active compound formulation having fungicidal, bactericidal, herbicidal, or antimycotic activity, which comprises an effective amount of the compound of claim 1 and an adhesive, a wetting agent, a dispersant, an emulsifier, a penetrating agent, a solvent, a filler, or a carrier.

10. A method of combatting fungi damaging crop plants which comprises treating the plants or the infected area thereof with a compound of claim 1.

11. A method of combatting fungi damaging crop plants which comprises treating the plants or the infected area thereof with a compound of claim 6.

* * * * *